United States Patent [19]

Celmer et al.

[11] 4,224,314

[45] Sep. 23, 1980

[54] ANTIBIOTICS PRODUCED BY SPECIES OF NOCARDIA

[75] Inventors: Walter D. Celmer, New London; Paul C. Watts, Mystic; Walter P. Cullen; Liang H. Huang, both of East Lyme, all of Conn.; Riichiro Shibakawa, Handa; Junsuke Tone, Chita, both of Japan

[73] Assignee: Pfizer Inc., New York, N.Y.

[21] Appl. No.: 16,961

[22] Filed: Mar. 2, 1979

[51] Int. Cl.³ .............................................. A61K 35/00
[52] U.S. Cl. .................................. 424/122; 424/115; 435/171
[58] Field of Search ............... 424/115, 122; 435/171; 195/81

[56] References Cited

U.S. PATENT DOCUMENTS 4,148,883  4/1979  Celmer et al. ..................... 424/122

*Primary Examiner*—Jerome D. Goldberg
*Attorney, Agent, or Firm*—Connolly and Hutz

[57] ABSTRACT

A species of Nocardia, designated *Nocardia argentinensis* Huang ATCC 31438, when subjected to aerobic submerged fermentation, produces an antibiotic complex containing as its major component antibiotic Compound 51,467. Methods for the recovery and purification of antibiotic Compound 51,467 and minor antibiotic components, Compounds 52,726 and 52,748, and some of their properties are outlined.

3 Claims, 3 Drawing Figures

*Infrared Absorption Spectrum Of Antibiotic Compound 52,726*

*Infrared Absorption Spectrum Of Antibiotic Compound 52,748*

ANTIBIOTICS PRODUCED BY SPECIES OF NOCARDIA

BACKGROUND OF THE INVENTION

The search for new antibiotics produced by soil microorganisms has encompassed the screening of various genera of bacteria and fungi including many species within each genus and many strains within each species.

Among the microorganisms that have received somewhat less attention than others are those that belong to the genus Nocardia. This genus has the narrow haphae of the Actinomycetales and is characterized by fragmentary substrate mycelium. The generic identity may be further supported by a cell wall of type IV as described by H. A. Lechevalier and M. P. Lechevalier, A Critical Evaluation of the Genera of Aerobic Actinomycetes, pages 393–405, in The Actinomycetales (1970), edited by H. Prauser and published by Fischer, Jena. This genus is further characterized by a whole-cell sugar pattern of type A as described by M. P. Lechevalier, Identification of Aerobic Actinomycetes of Clinical Importance, J. Lab. Clin. Med., 71(6), 934–944 (1968).

SUMMARY OF THE INVENTION

This invention is concerned with a mixture of antibiotics, containing as its major component antibiotic Compound 51,467, produced under submerged aerobic fermentation conditions by *Nocardia argentinensis* Huang ATCC 31438.

DETAILED DESCRIPTION OF THE INVENTION

Figure 1:
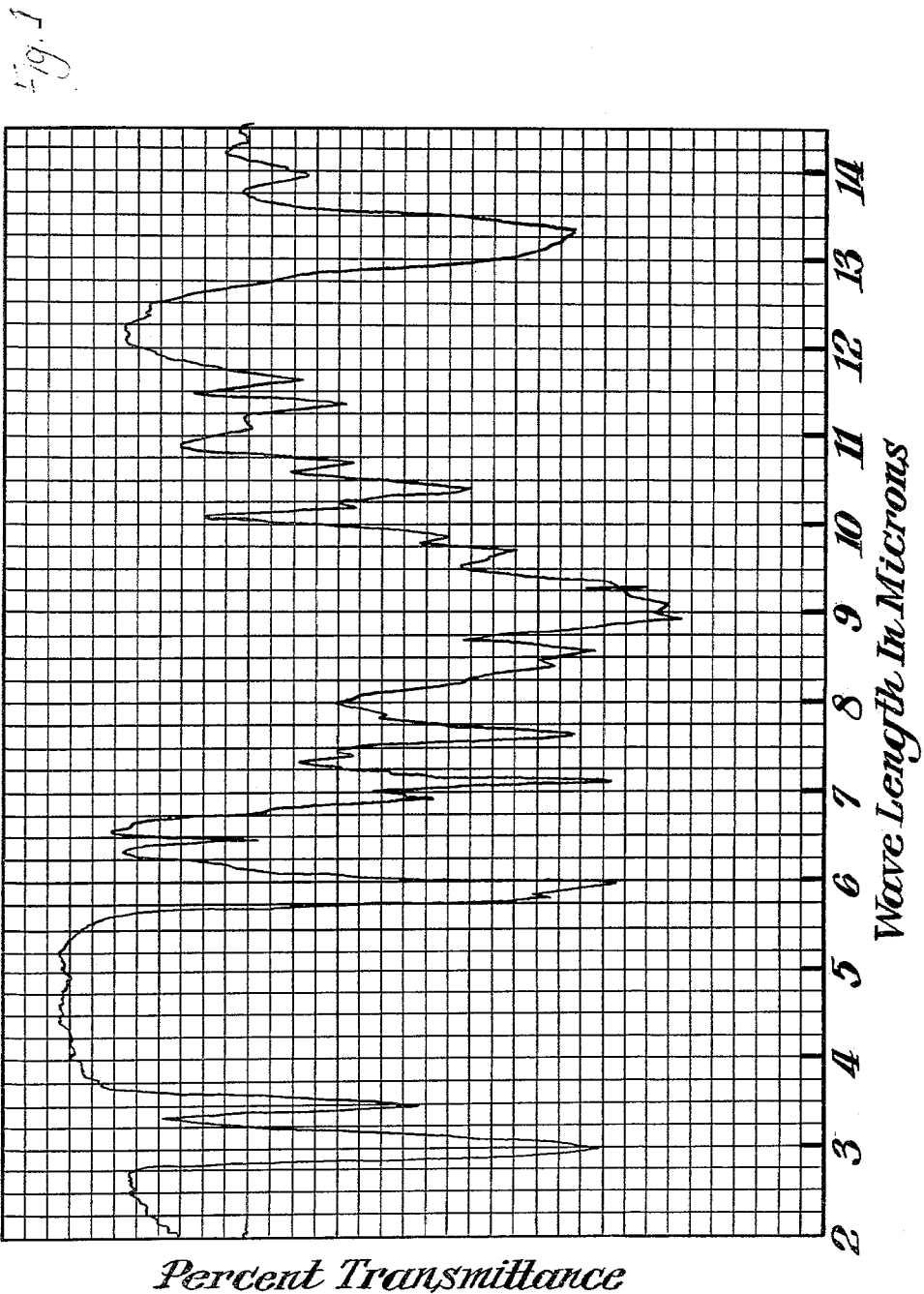

The microorganism useful for the preparation of the antibiotics of this invention was isolated from a soil sample from Hollywood, Calif., U.S.A. This culture, designated a new strain of *Nocardia argentinensis* Huang, has been deposited in The American Type Culture Collection, Rockville, Md. as the type culture under their accession number ATCC 31438. The permanency of the deposit of this culture at The American Type Culture Collection at Rockville, Md. and ready accessibility thereto by the public are afforded throughout the effective life of the patent in the event the patent is granted. Access to the culture is available during pendency of the application under 37 CFR 1.14 and 35 USC 112. All restrictions on the availability to the public of the culture deposited will be irrevocably removed upon granting of the patent.

The culture was planted from a slant into liquid ATCC No. 172 medium and grown for 4 days at 28° C. on a shaker. It was then homogenized for 30 seconds in a blender, centrifuged for 20 minutes, washed three times with sterile distilled water and planted on media commonly used for identification of members of the Actinomycetales.

The inoculated media were incubated at 28° C. and records of results were made after suitable incubation time with most final results recorded at a period of 14 days. The colors were described in common terminology, but exact color was determined by comparison with color chips from the Color Harmony Manual, fourth edition. About 10 grams of washed, autoclaved mycelium of the culture were used for mycolated analyses. The methods of whole-cell, sugar and lipid analyses are those described by Becker, B., Lechevalier, M. P., Gordon, R. E., and Lechavalier, H. A., "Rapid Differentiation between Nocardia and Streptomyces by Paper Chromatography of Whole-Cell Hydrolysates," App. Microbiol., 12, 421–423 (1964); Lechevalier, M. P., "Identification of Aerobic Actinomycetes of Clinical Importance," J. Lab. Clin., Med., 71, 934–944 (1968); and Lechavalier, M. P. et al., lipid composition in the classification of Nocardiae and Mycobacteria, J. Bacteriol., 105, 313–318 (1971).

Identification media used for the characterization of the culture and references for their composition are as follows:

1. Tryptone Yeast Extract Broth (ISP #1 medium, Difco).
2. Yeast Extract—Malt Extract Agar (ISP #2 medium, Difco).
3. Oatmeal Agar (ISP #3 medium, Difco).
4. Inorganic Salts—Starch Agar (ISP #4 medium, Difco).
5. Glycerol—Asparagine Agar (ISP #5 medium, Difco).
6. Peptone—Yeast Extract Iron Agar (ISP #6 medium, Difco).
7. Gelatin Agar—R. E. Gordon and J. M. Mihm, Jr. Bact. 73: 15–27, 1957.
8. Starch Agar—Ibid.
9. Organic Nitrate Broth—Ibid.
10. Dextrose Nitrate Broth—S. A. Waksman, The Actinomycetes, Vol. 2, medium no. 1, p. 328, 1961, and 3 g dextrose substituted for 30 g sucrose and agar omitted.
11. Potato Carrot Agar—M. P. Lechevalier, Jr. Lab. and Clinical Med. 71: 934–944, 1968 but use only 30 g potatoes, 2.5 g carrots and 20 g agar.
12. 2% Tap Water Agar.
13. Czapek-Sucrose Agar—S. A. Waksman, The Actinomycetes, Vol. 2, medium no. 1, p. 328, 1961.
14. Glucose Asparagine Agar—Ibid, medium no. 2, p. 328.
15. Glucose-Yeast Extract Agar—Ibid, Medium no. 29, p. 331.
16. Emerson's Agar—Ibid, medium no. 28, p. 331.
17. Nutrient Agar—Ibid, medium no. 14, p. 330.
18. Bennett's Agar—Ibid, medium no. 30, p. 331.
19. Gordon and Smith Tyrosine Agar—R. E. Gordon and M. M. Smith, Jr. Bact. 69: 147–150, 1955.
20. Casein Agar—Ibid.
21. Calcium Malate Agar—S. A. Waksman, Bact. Rev. 21: 1–29, 1957.
22. Skim Milk—Difco.
23. Cellulose Utilization—
   (a) H. L. Jensen, Proc. Linn. Soc. N.S.W. 55: 231–248, 1930.
   (b) M. Levine and H. W. Schoenlein, A Compilation of Culture Media, medium 2511, 1930.
24. Utilization of Organic Acids—R. E. Gordon et al., Int. Jr. Syst. Bact. 24: 54–63, 1974.
25. Carbohydrate Utilization and Acid Production from Carbohydrates—Ibid.
26. Hydrolysis of Hippurate and Esculin—Ibid.
27. Decomposition of Adenine, Hypoxanthine, Xanthine, and Urea—Ibid.
28. Yeast Dextrose Agar for Studies of Temperature, Resistance to Penicillin and Survival at 50° C.—Ibid.
29. Resistance to Lysozyme—Ibid.
30. Glucose Broth—Ibid.

The culture, a new strain of *Nocardia argentinensis* Huang, described as follows on the various culture media:

Yeast Extract-Malt Extract Agar—Growth good, white to grayish (2 fe to 2 ih), raised, smooth to wrinkled, with white or grayish aerial mycelium; reverse pale yellowish (2 ga), pale orange (4 ia) to black; no soluble pigment.

Oatmeal Agar—Growth poor to moderate; pale whitish, thin, smooth, with some white specks of aerial mycelium; reverse same as surface; no soluble pigment.

Inorganic Salts-Starch Agar—Growth poor to moderate, pale white, thin, smooth, with a few small specks of white aerial mycelium; reverse colorless; no soluble pigment.

Glycerol-Asparagine Agar—Growth poor to moderate, cream (1½ ca), thin, smooth, with a few specks of cream aerial mycelium; reverse colorless to cream; no soluble pigment.

Gelatin Agar—Growth good, off-white, slightly raised, smooth but wrinkled near the edge, with short off-white aerial mycelium; reverse pale yellowish orange (3 ea); no soluble pigment.

Starch Agar—Growth good, off-white, thin, smooth to slightly wrinkled, with off-white aerial mycelium; reverse pale yellowish orange (near 3 ea); no soluble pigment.

Potato Carrot Agar—Growth poor to moderate, white with pale orange tint (3 ea), thin, smooth, with a few dots of white aerial mycelium; reverse same as surface; no soluble pigment.

Tap Water Agar—Growth poor, colorless, thin, smooth, no aerial mycelium; reverse colorless; no soluble pigment.

Czapek-Sucrose Agar—Growth poor to moderate, pale white, thin, smooth, with some specks of white aerial mycelium; reverse colorless to cream; no soluble pigment.

Glucose Asparagine Agar—Growth moderate to good, whitish orange to yellowish orange (3 ea to 3 la), slightly raised, smooth to wrinkled, no aerial mycelium; reverse same as surface; no soluble pigment.

Glucose Yeast Extract Agar—Growth good, off-white to pale grayish (2 ec) raised, wrinkled, with pale grayish aerial mycelium; reverse pale yellowish orange (near 3 ga) with a few gray to black specks; with pale yellowish soluble pigment.

Emerson's Agar—Growth good to excellent, pink to pinkish orange (5 ca to 5 da), raised, wrinkled to furrowed, with white aerial mycelium; reverse brownish orange (4 na); with pale brown soluble pigment (3 lc).

Nutrient Agar—Growth moderate, pale white to white, thin, smooth, with no to scant aerial mycelium; reverse pale yellowish (2 ea to 2 ga); no soluble pigment.

Bennett's Agar—Growth good, lavender to dark lavender (7 ec, 7 ge, 7 lg to 7 li), raised, wrinkled, with lavender to dark lavender aerial mycelium; reverse pale orange (4 ga) to black; with no to very pale yellowish soluble pigment.

Gordon and Smith Tyrosine Agar—Growth good, white with grayish (2 ig) dots, moderately raised, smooth but wrinkled near the edge, with white or grayish aerial mycelium; reverse pale yellowish orange (3 ea); no soluble pigment.

Casein Agar—Growth good, white but pale yellowish near the edge, raised, wrinkled, with short aerial mycelium; reverse colorless; soluble pigment pale orange (near 3 ia).

Calcium Malate Agar—Growth moderate, off-white with pale orange (3 ea) dots, thin, smooth, with some aerial mycelium; reverse same as surface; no soluble pigment.

Morphological Properties

Morphological observations were made 8 hr or once every day up to 5 days after the inoculation of the culture on Czapek-sucrose agar: Substrate mycelium beginning to fragment into bacillary cells after 4-day incubation; aerial mycelium short, often zig-zagged, may fragment into bacillary cells as the culture ages; the hyphae fragment into short rods to rods which are smooth and measure $0.9-2(-3) \times 0.7-0.9$ μm.

Biochemical Properties

I. Gram-positive; non-acid-fast; melanin production negative; production of hydrogen sulfide negative; nitrate reduction positive, gelatin liquefaction positive; hydrolysis of exculin positive; hydrolysis of hippurate and starch negative; decomposition of adenine and xanthine negative; decomposition of casein, hypoxanthine, tyrosine, and urea positive; decomposition of cellulose negative; resistance to lysozyme and penicillin positive; clearing but no coagulation on milk. Decomposition of calcium malate positive.

II. Utilization of organic acids: acetate, citrate, lactate, malate, propionate, pyruvate and succinate utilized; benzoate, mucate, oxalate, dextrin and phenol not utilized.

III. Acid production from carbohydrates: Acid produced from fructose, glucose, glycerol, inositol, ribose, salicin and trehalose; acid not produced from adonitol, arabinose, cellobiose, dulcitol, erythritol, galactose, lactose, maltose, mannitol, mannose, melezitose, melibiose, methyl-d-glucoside, raffinose, rhamnose, sorbitol, sorbose, starch, sucrose and xylose.

IV. Carbohydrate utilization: Fructose, glucose, glycerol, inositol, maltose, ribose, salicin, sucrose and trehalose utilized; starch and mannose doubtfully utilized to utilized; cellobiose, lactose, mannitol, melezitose, methyl-d-glucoside, raffinose, sorbitol and xylose doubtfully utilized; adonitol, arabinose, dulcitol, erythritol, galactose and rhamnose not utilized. Utilization of melibiose and sorbose doubtful.

Temperature Relations: Culture grows at 5°, 21°, 28° and 37° C., but not at 45° C. Culture failed to survive at 50° C. for 8 hours.

Cell Wall Analyses: The cell wall contains meso-diaminopimelic acid, arabinose and galactose.

Mycolate Analyses: The mycolates are of nocardomycolate type-on pyrolysis, major amounts of $n-C_{16}$ and $n-C_{18}$ fatty acid methyl esters and very minor amounts of $n-C_{14}$ and $n-C_{12}$ methyl esters are released.

The presence of meso-diaminopimelic acid, arabinose, galactose, and nocardomycolates in the cell wall placed the culture in the genus Nocardia. The culture was Gram-positive, non-acid fast, and characterized by the fragmentation of substrate mycelium after 4 days of incubation. The general biochemical properties coincided with the species *Nocardia argentinensis* Huang described in co-pending application, Ser. No. 825,563, filed Aug. 18, 1977 now U.S. Pat. No. 4,148,883.

Since cultural variation is common among strains of Nocardia species, the culture is considered to be a new strain of *Nocardia argentinensis*.

Cultivation of *Nocardia argentinensis* ATCC 31438 preferably takes place in aqueous nutrient media at a temperature of 24°–36° C. and under submerged aerobic conditions with agitation. Nutrient media which are useful for such purposes include a source of assimilable carbon such as sugars, starches and glycerol; a source of organic nitrogen such as casein, enzymatic digest of casein, soybean meal, cotton seed meal, peanut meal, wheat gluten, soy flour, meat meal and fish meal. A source of growth substances such as grain solubles and yeast extract as well as salts such as sodium chloride and calcium carbonate and trace elements such as iron, zinc, cobalt and manganese may also be utilized with advantageous results. If excessive foaming is encountered during fermentation, antifoam agents such as vegetable oils or silicones may be added to the fermentation medium. Aeration of the medium in tanks for submerged growth is preferably maintained at the rate of about ½ to 2 volumes of free air per volume of broth per minute. Agitation may be maintaind by means of agitators generally familiar to those in the fermentation industry. Aseptic conditions must, of course, be maintained through the transfer of the organism and throughout its growth.

Inoculum for the preparation of the antibiotic may be obtained by employing growth from a slant of the culture. The growth may be used to inoculate either shake flasks or inoculum tanks or the inoculum tanks may be seeded from the shake flasks. Growth in shaken flasks will generally have reached its maximum in 2 to 4 days whereas inoculum is submerged inoculum tanks will usually be at the most favorable period in 1.5–3 days. Substantial antibiotic activity is obtained in the final fermentor stage in approximately 2 to 5 days.

The process of antibiotic production is conveniently followed during fermentation by biological assay of the broth employing a sensitive strain of *Staphylococcus aureus* or *Micrococcus luteus*. Standard plate assay technique is employed in which the zone of inhibition surrounding a filter paper disc saturated with broth is used as a measure of antibiotic potency.

Thin-layer chromatography employing silica gel is a useful tool for analyzing the antibiotics produced by *Nocardia argentinensis* ATCC 31438 in fermentation media and the composition of crude and purified materials extracted from fermentation broths. Silica gel plates are employed with a developing system of chloroform: acetone (3:1 v/v). These antibiotics may be visualized by exposure to 254 nm light or bio-overlay with a thin layer of agar seeded with a sensitive strain of *Staphylococcus aureus* or *Micrococcus luteus*.

The antibiotics may be separated and recovered by extracting the whole, unfiltered fermentation broth with an organic solvent such as chloroform, ethyl acetate, methylisobutyl ketone or butanol at a pH range of 4.0 to 10.0. The solvent is concentrated to a thin syrup, defatted with heptane and chromatographed in chloroform on silica gel.

A method of separation and purification of antibiotic Compound 51,467 is as follows: Whole fermentation broth is extracted with ethyl acetate. The solvent extract is then concentrated in vacuo. The dark oily residue is triturated with heptane and a dispersion of the viscous concentrate in heptane is transferred to a sintered glass filter containing silica gel. The silica gel is washed successively with heptane, heptane-chloroform, chloroform, chloroform-methanol, and finally methanol. All steps in the purification sequence are monitored by thin-layer chromatography and 254 nm ultraviolet light. The bulk of the weight and activity are in the final volumes of solvent wash. The solvent is removed in vacuo and the viscous oil is passed down a column of a hydroxypropylated dextran gel (Sephadex LH-20, Pharmacia Fine Chemicals, Piscataway, N.J.) in methanol. The oil obtained by solvent removal is dissolved in ethyl acetate and decolorized by stirring with activated carbon (Darco G-60). The pale yellow foam produced is chromatographed on a silica gel column made up in chloroform and eluted with chloroform-methanol with increasing amounts of methanol. Appropriate fractions are combined to yield essentially pure Compound 51,467 as an amorphous white solid.

The present invention includes within its scope the dilute forms and crude concentrates of the mixture of antibiotics and the purified antibiotic Compound 51,467. The minor antibiotics are present in such small amounts that it has not proved possible to isolate all of them in a state of homogeneity at the present time. All of these compositions are useful in combating microorganisms, especially strains of *Staphylococcus aureus* that are resistant to other antibiotics.

Table I illustrates the antibacterial spectrum of Compound 51,467. These tests were run by preparing tubes of nutrient broth with gradually increasing concentrations of the pure antibiotic and then seeding the broths with the particular organism specified. The minimal inhibitory concentration indicated in Table I is the minimal concentration of the antibiotic (in micrograms/ml) at which the microorganism failed to grow. The tests were conducted under standardized conditions as described in Proc. Soc. Exp. Biol. & Med., 122, 1107 (1966).

TABLE I

| Organism | Compound 51,467 (mcg/ml) |
|---|---|
| *Staphylococcus aureus* | |
| 01A005 | 0.78 |
| 01A052 | 0.78 |
| 01A109 | 0.39 |
| 01A110 | 1.56 |
| 01A400 | 0.39 |
| *Staphylococcus epidermidis* | |
| 01B087 | 6.25 |
| 01B111 | 1.56 |
| 01B126 | 1.56 |
| *Streptococcus faecalis* | |
| 02A006 | >200 |
| *Streptococcus agalactiae* | |
| 02B006 | >200 |
| *Streptococcus pyrogenes* | |
| 02C000 | >200 |
| 02C203 | >200 |
| *Pseudomonas aeruginosa* | |
| 52A104 | >200 |
| *Klebsiella pneumoniae* | |
| 53A009 | >200 |
| 53A031 | >200 |
| *Salmonella typhimurium* | |
| 58D009 | >200 |
| *Pasteurella multocida* | |
| 59A001 | >200 |
| *Enterobacter aerogenes* | |
| 67A040 | >200 |
| *Escherichia coli* | |
| 51A266 | >200 |
| 51A470 | 12.5 |

In vivo protection afforded by Compound 51,467 against mice experimentally infected with *Staphylococcus aureus* 01A005 is shown in Table II.

TABLE II

| Compound 51,467 Dose (mg/kg) | Protection (%) Oral | Subcutaneous |
|---|---|---|
| 200 | 80 | |
| 100 | 0 | |
| 50 | 0 | 70 |
| 12.5 | | 20 |
| 3.12 | | 10 |

Antibiotic Compound 51,467 can be administered via the oral or parenteral routes for the treatment in animals, including humans, of staphylococcal and other antibiotic-sensitive infections. In general, the antibiotic is most desirably administered in daily oral doses of 0.5 to 1 gram or parenteral injections of 100 to 500 mg., depending on the type and severity of the infection and weight of the subject being treated.

Antibiotic Compound 51,467 may be administered alone or in combination with pharmaceutically-acceptable carriers, and such administration can be carried out in both single and multiple doses.

For purposes of oral administration, tablets containing various excipients such as sodium citrate, calcium carbonate and dicalcium phosphate may be employed along with various disintegrants such as starch, alginic acid and certain complex silicates together with binding agents such as polyvinylpyrrolidone, sucrose, gelatin and gum acacia. Additionally, lubricating agents such as magnesium stearate, sodium lauryl sulfate and talc are often useful for tableting purposes. Solid compositions of a similar type may also be employed as fillers in soft and hard-filled gelatin capsules; preferred materials include lactose as well as high molecular weight polyethylene glycols. When aqueous suspension and/or elixirs are desired for oral administration, the essential active ingredient therein may be combined with various sweetening or flavoring agents, coloring matter or dyes, and if desired, emulsifying and/or suspending agents as well, together with such diluents as water, ethanol, propylene glycol, glycerol and various combinations thereof.

For purpose of parenteral administration, solutions of Compound 51,467 or solutions of a mixture of the antibiotics produced by *Nocardia argentinensis* ATCC 31438 in sesame or peanut oil or in aqueous propylene glycol may be employed.

EXAMPLE I

A sterile aqueous medium having the following composition was prepared:

| Ingredient | Grams/liter |
|---|---|
| Glucose | 10 |
| Soluble starch | 20 |
| Yeast extract | 5 |
| Enzymatic digest of casein | 5 |
| Dipotassium hydrogen phosphate | 0.5 |
| Meat meal | 5 |
| Cobalt chloride | 0.002 |
| Calcium carbonate | 4 |
| pH 7.1–7.2 | |

Cells from a slant culture of *Nocardia argentinensis* ATCC 31438 were transferred to each of a number of 300 ml shake flasks each containing 40 ml of the above medium and shaken at 28° C. for three to four days.

A sterile aqueous medium having the following composition was prepared:

| Ingredient | Grams/liter |
|---|---|
| Glucose | 1.0 |
| Enzymatic digest of casein | 2.5 |
| Soluble starch | 5.0 |
| Corn steep liquor | 5.0 ml |
| Calcium carbonate | 3.0 |
| Cobalt chloride | 0.002 |
| pH 6.9–7.0 | |

Fermentors containing two liters of the above described sterile medium were seeded with 2-4% v/v of grown inoculum. The temperature was maintained at 30° C. The broth was stirred at 1700 r.p.m. and aerated at the rate of about one volume of air per volume of broth per minute. When substantial antibiotic activity was obtained (based on antibiotic disc assay), ca. 2-5 days, the filtered or whole fermentation broth was twice extracted with ⅛ to ¼ volume of methylisobutyl ketone. The solvent was separated from the aqueous phase and concentrated in vacuo to a viscous oil.

EXAMPLE II

The fermentation process of Example I may be repeated employing the following fermentation medium:

| Ingredient | Grams/liter |
|---|---|
| Dextrin | 20 |
| Soybean flour | 10 |
| Distiller's solubles | 1 |
| Ferrous sulfate | 0.1 |
| pH 6.9–7.1 | |

EXAMPLE III

The fermentation process of Example I may be repeated employing the following fermentation medium:

| Ingredient | Grams/liter |
|---|---|
| Glucose | 10 |
| Soluble starch | 20 |
| Yeast extract | 5 |
| Enzymatic digest of casein | 5 |
| Calcium carbonate | 1 |
| Cobalt chloride | 0.002 |
| pH 6.9–7.1 | |

EXAMPLE IV

The fermentation process of Example 1 was repeated. About 0.1% v/v of the grown inoculum was used to inoculate a 2000 gallon fermentor containing 1200 gallons of the production medium of Example I. The fermentation was conducted at a temperature of 28° C. and an aeration rate of one volume of air per volume of broth per minute. After substantial antibiotic activity was obtained (approximately 48-72 hours), about 1000 gallons of the whole fermentation broth, pH 8.2, was extracted with approximately 350 gallons of ethyl acetate. Concentration of the solvent extract in vacuo gave rise to a dark oily residue. This residue was triturated in several stages utilizing approximately two gallons of heptane. The heptane insoluble material (approximately 600 grams) was batch treated by dispersion on approximately 1200 grams of silica gel 60 (E. Merck, Darmstadt, Germany) in the presence of heptane and added to a 2.0 liter sintered glass funnel containing approximately 400 grams of silica gel 60. It was then washed successively with 1.0 liter heptane; 1.0 liter heptane-chloroform 1:1; 1.0 liter chloroform (4×); 1.0 liter methanol-chloroform 1:1, and finally 1.0 liter methanol. All steps were monitored using thin-layer chromatography and 254 nm ultraviolet light. The bulk of the weight and activity were contained in the last three liters of solvent wash. A total of approximately 350 grams of viscous oil was obtained. This oil was then passed down a Sephadex LH-20 column in methanol. Concentration of all bio-active material gave 40.5 grams of oil. This was again passed down a Sephadex LH-20 column to yield 30 grams of a red-orange gum. This gum was dissolved in 300 ml of ethyl acetate and decolorized by stirring with 15 grams of Darco G-60 activated carbon. Twenty-eight grams of a pale yellow foam was produced. This material was then chromatographed on approximately 1600 grams of silica gel H, made up in chloroform, and eluted with chloroform-methanol, with increasing amounts of methanol up to 5%. Appropriate fractions from the column were combined to yield essentially pure Compound 51,467 (approximately 21 grams) as an amorphous white solid.

Compound 51,467 (sample dried overnight in vacuo 45°–50° C.)

Elemental Analysis. C, 57.27; H, 6.42; N, 2.37; O, 33.94 (by difference).

Molecular Formula $C_{29}H_{39}O_{10}N$ (M+ = 561). The $^{13}C$ nmr spectrum displays resonance consistent with the presence of twenty nine carbon atoms.

Optical Rotation $[\alpha]_D^{25°} = +80.9°$ (c = 1.0, methanol)

Ultraviolet Light Absorption Maxima $\lambda_{max}^{MeOH}$ 264 nm; $E_1{}_{cm}{}^{1\%}$ 277.

Characteristic Infrared Bands (KBr disc) in microns as shown in FIG. 1:
2.90, 3.42, 5.75, 5.90, 6.40, 6.90, 7.05, 7.58, 8.50, 8.90, 9.70, 10.35, 11.35, 11.60 and 13.25.

Solubilities

Soluble in methanol, ethanol, chloroform and ethyl acetate.

Insoluble in heptane and water.

Compound 51,467 ($C_{29}H_{39}O_{10}N$) was determined to be an analogue of Compound 47,444 ($C_{28}H_{37}O_8N$) produced by *Nocardia argentinensis* ATCC 31306 as described in copending application Ser. No. 825,563, filed Aug. 18, 1977.

Careful fractionation of other column cuts yielded very small amounts of antibiotic Compound 52,726 (off-white amorphous solid, m.p. 116°–124° C.) and antibiotic Compound 52,748 (off-white amorphous solid).

Compound 52,726 (sample dried overnight in vacuo 45°–50° C.)

Molecular Formula $C_{28}H_{37}O_9N$ (Molecular Weight = 531)

Ultraviolet Light Absorption Maxima $\lambda_{max}^{MeOH}$ = 265 nm.

Figure 2:
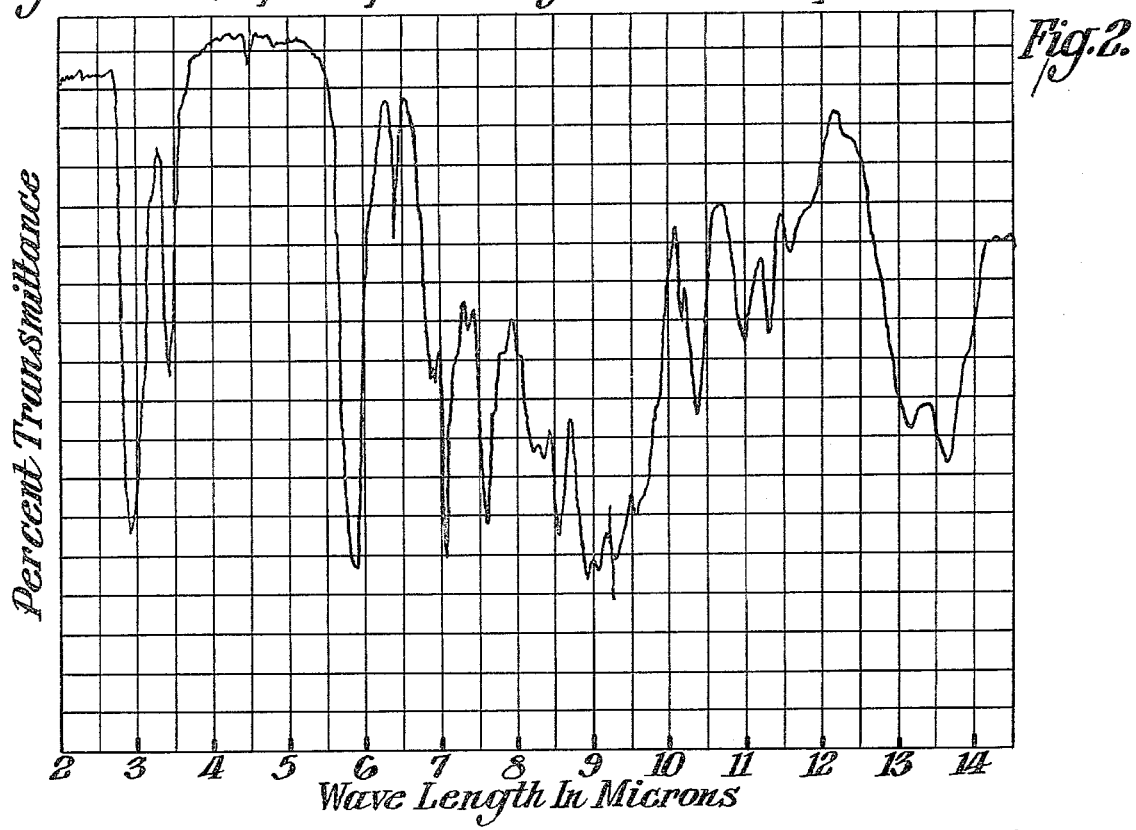

Characteristic Infrared Bands (KBr disc) in micron as shown in FIG. 2:
2.92, 3.40, 5.85, 6.40, 7.08, 7.60, 8.60, 8.90, 10.35, 11.00, 11.30, 13.20 and 13.65.

Solubilities

Soluble in methanol, ethanol, chloroform and ethyl acetate. Insoluble in heptane and water.

Compound 52,748

Figure 3:
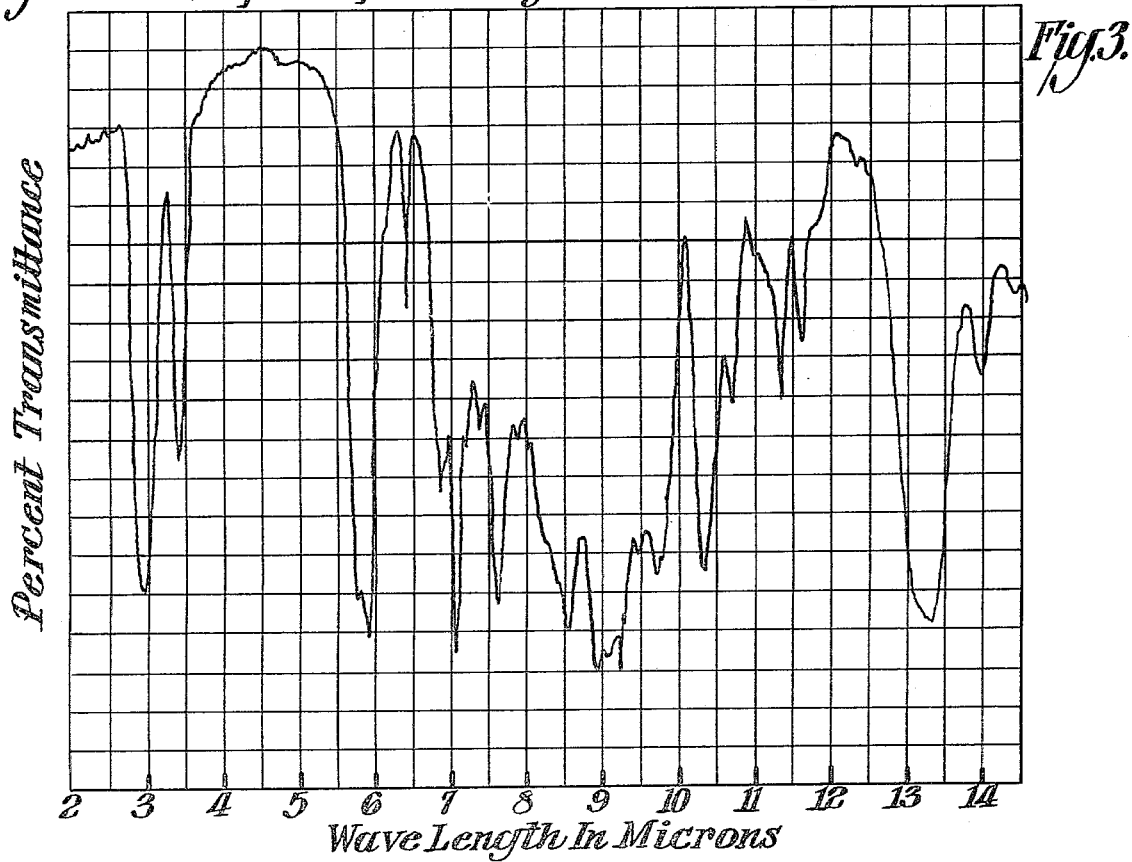

This compound is an isomer of Compound 52,726 with the same molecular weight (531) and same molecular formula ($C_{28}H_{37}O_9N$). The solubilities of the two compounds are the same. Infrared bands (KBr disc) in microns are shown in FIG. 3: 2.92, 3.40, 5.78, 5.90, 6.40, 7.08, 7.60, 8.55, 8.90, 10.30, 11.30, 11.60, 13.30 and 14.00.

What is claimed is:

1. An antibiotic mixture produced by cultivating *Nocardia argentinensis* Huang ATCC 31438 under submerged aerobic conditions in an aqueous nutrient medium containing an assimilable source of carbon and nitrogen until substantial antibiotic activity is obtained and separating said antibiotic mixture therefrom.

2. Antibiotic Compound 51,467 which is soluble in methanol, ethanol, chloroform and ethyl acetate; insoluble in heptane and water; has an ultraviolet light absorption maximum at 264 nm with $E_1{}_{cm}{}^{1\%}$ value of 277; has the molecular formula of $C_{29}H_{39}O_{10}N$; has an optical rotation of $[\alpha]_D^{25} = +80.9°$ at a concentration of 1% in methanol; and when pelleted in KBr, exhibits characteristic absorption in the infrared region at the following wavelengths in microns: 2.90, 3.42, 5.75, 5.90, 6.40, 6.90, 7.05, 7.58, 8.50, 8.90, 9.70, 10.35, 11.60 and 13.25.

3. A pharmaceutical composition suitable for combating bacterial infections comprising a pharmaceutically acceptable carrier and a therapeutically-effective antistaphylococcal amount of Compound 51,467 as defined in claim 2.

* * * * *